(12) United States Patent
Weiner et al.

(10) Patent No.: US 7,067,335 B2
(45) Date of Patent: Jun. 27, 2006

(54) APPARATUS AND METHODS FOR SEMICONDUCTOR IC FAILURE DETECTION

(75) Inventors: Kurt H. Weiner, San Jose, CA (US); Gaurav Verma, Atherton, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/264,625

(22) Filed: Oct. 2, 2002

(65) Prior Publication Data

US 2003/0071261 A1    Apr. 17, 2003

Related U.S. Application Data

(63) Continuation-in-part of application No. 09/648,380, filed on Aug. 25, 2000, now Pat. No. 6,528,818.

(60) Provisional application No. 60/329,804, filed on Oct. 17, 2001.

(51) Int. Cl.
*G01R 31/26* (2006.01)
*H01L 21/66* (2006.01)

(52) U.S. Cl. ............... 438/16; 324/765

(58) Field of Classification Search ........ 438/10, 438/11, 16, 17, 18, 12, 13; 324/765, 751, 324/537; 257/48
See application file for complete search history.

(56) References Cited

U.S. PATENT DOCUMENTS 3,808,527 A * 4/1974 Thomas ............... 324/716

(Continued)

FOREIGN PATENT DOCUMENTS

EP    0 853 243 A2    7/1998

(Continued)

OTHER PUBLICATIONS

Tugbawa, et al, "Pattern And Process Dependencies In Copper Damascene Chemical Mechanical Polishing Processes," Jun. 1998, VLSI Multilevel Interconnect conference (VMIC).

(Continued)

*Primary Examiner*—Hoai Pham
*Assistant Examiner*—Dana Farahani
(74) *Attorney, Agent, or Firm*—Beyer Weaver & Thomas, LLP

(57) ABSTRACT

An improved voltage contrast test structure is disclosed. In general terms, the test structure can be fabricated in a single photolithography step or with a single reticle or mask. The test structure includes substructures which are designed to have a particular voltage potential pattern during a voltage contrast inspection. For example, when an electron beam is scanned across the test structure, an expected pattern of intensities are produced and imaged as a result of the expected voltage potentials of the test structure. However, when there is an unexpected pattern of voltage potentials present during the voltage contrast inspection, this indicates that a defect is present within the test structure. To produce different voltage potentials, a first set of substructures are coupled to a relatively large conductive structure, such as a large conductive pad, so that the first set of substructures charges more slowly than a second set of substructures that are not coupled to the relatively large conductive structure. Mechanisms for fabricating such a test structure are also disclosed. Additionally, searching mechanisms for quickly locating defects within such a test structure, as well as other types of voltage contrast structures, during a voltage contrast inspection are also provided.

11 Claims, 6 Drawing Sheets

U.S. PATENT DOCUMENTS

| | | | |
|---|---|---|---|
| 4,644,172 A | 2/1987 | Sandland et al. | 250/548 |
| 4,902,967 A | 2/1990 | Flesner | 324/158 R |
| 5,489,852 A | 2/1996 | Gomez | 324/754 |
| 5,502,306 A | 3/1996 | Meisburger et al. | 250/310 |
| 5,537,669 A | 7/1996 | Evans et al. | 382/141 |
| 5,578,821 A | 11/1996 | Meisberger et al. | 250/310 |
| 5,665,968 A | 9/1997 | Meisburger et al. | 250/310 |
| 5,717,204 A | 2/1998 | Meisburger et al. | 250/310 |
| 5,804,459 A | 9/1998 | Bolam et al. | 438/12 |
| 5,959,459 A | 9/1999 | Satya et al. | 324/751 |
| 5,978,795 A * | 11/1999 | Poutanen et al. | 707/3 |
| 6,021,214 A | 2/2000 | Evans et al. | 382/141 |
| 6,061,814 A | 5/2000 | Sugasawara et al. | 714/724 |
| 6,091,249 A | 7/2000 | Talbot et al. | 324/751 |
| 6,163,159 A * | 12/2000 | Seyama | 324/751 |
| 6,252,412 B1 | 6/2001 | Talbot et al. | 324/750 |
| 6,265,232 B1 | 7/2001 | Simmons | 438/14 |
| 6,292,582 B1 | 9/2001 | Lin et al. | 382/149 |
| 6,294,397 B1 * | 9/2001 | Jarvis et al. | 438/17 |
| 6,324,298 B1 | 11/2001 | O'Dell et al. | 382/149 |
| 6,344,750 B1 | 2/2002 | Lo et al. | 324/751 |
| 6,348,690 B1 | 2/2002 | Iwabuchi et al. | 250/310 |
| 6,426,516 B1 * | 7/2002 | Sloman | 257/48 |
| 6,452,412 B1 | 9/2002 | Jarvis et al. | 324/765 |
| 6,528,818 B1 | 3/2003 | Satya et al. | 257/48 |
| 6,583,413 B1 | 6/2003 | Shinada et al. | 250/310 |

FOREIGN PATENT DOCUMENTS

| | | |
|---|---|---|
| EP | 0 892 275 A2 | 1/1999 |
| WO | WO 99/22310 | 5/1999 |
| WO | WO 99/22311 | 5/1999 |

OTHER PUBLICATIONS

Park et al, "Multi-Level Pattern Effects In Copper CMP," Oct 1999, CMP Symposium Electrochemical Society Meeting.

Weiner, et al. "Apparatus and Methods for Monitoring Self-Aligned Contact Arrays", U.S. Appl. No. 09/999,843, filed on Oct. 24, 2001.

Weiner, et al. "Apparatus and Methods for Reliable and Efficient Detection of Voltage Contrast Defects", U.S. Appl. No. 10/000,114, filed on Oct. 30, 2001.

Satya, et al., "Test Structures and Methods for Inspection of Semiconductor Integrated Circuits", U.S. Appl. No. 09/648,380, filed on Aug. 25, 2001.

* cited by examiner

APPARATUS AND METHODS FOR SEMICONDUCTOR IC FAILURE DETECTION

CROSS REFERENCE TO RELATED APPLICATIONS

This application is a continuation-in-part and claims priority of U.S. patent application Ser. No. 09/648,380, entitled TEST STRUCTURES AND METHODS FOR INSPECTION OF SEMICONDUCTOR INTEGRATED CIRCUITS, filed Aug. 25, 2000, by Akella V. S. Satya et al., which application is incorporated herein by reference in its entirety for all purposes.

This application also claims priority of the U.S. Provisional Application, having an application No. 60/329,804, entitled APPARATUS AND METHODS FOR SEMICONDUCTOR IC FAILURE DETECTION, filed Oct. 17, 2001, by Kurt H. Weiner et al., which application is incorporated herein by reference in its entirety for all purposes.

BACKGROUND OF THE INVENTION

This invention relates to methods and apparatus for detecting electrical defects in a semiconductor device or test structure having a plurality of features that are specifically designed to produce varying voltage potentials during a voltage contrast inspection. More particularly, it relates to voltage contrast techniques for detecting open and short type defects within the features of the circuit or test structure.

A voltage contrast inspection of a test structure is accomplished with a scanning electron microscope. The voltage contrast technique operates on the basis that potential differences in the various locations of a sample under examination cause differences in secondary electron emission intensities when the sample is the target of an electron beam. The potential state of the scanned area is acquired as a voltage contrast image such that a low potential portion of, for example, a wiring pattern might be displayed as bright (intensity of the secondary electron emission is high) and a high potential portion might be displayed as dark (lower intensity secondary electron emission). Alternatively, the system may be configured such that a low potential portion might be displayed as dark and a high potential portion might be displayed as bright.

A secondary electron detector is used to measure the intensity of the secondary electron emission that originates from the path swept by the scanning electron beam. Images may then be generated from these electron emissions. A defective portion can be identified from the potential state or appearance of the portion under inspection. The portion under inspection is typically designed to produce a particular potential and resulting brightness level in an image during the voltage contrast test. Hence, when the scanned portion's potential and resulting image appearance differs significantly from the expected result, the scanned portion is classified a defect.

Several inventive test structures designed by the present assignee are disclosed in co-pending U.S. patent application Ser. No. 09/648,380, entitled TEST STRUCTURES AND METHODS FOR INSPECTION OF SEMICONDUCTOR INTEGRATED CIRCUITS, filed Aug. 25, 2000, by Akella V. S. Satya et al., which application is incorporated herein by reference in its entirety. In one embodiment, a test structure is designed to have alternating high and low potential conductive lines during a voltage contrast inspection. In one inspection application, the low potential lines are at ground potential, while the high potential lines are at a floating potential. If a line that is meant to remain floating shorts to an adjacent grounded line, both lines will now produce a low potential during a voltage contrast inspection. If there is an open defect present within a line that is supposedly coupled to ground, this open will cause a portion of the line to be left at a floating potential to thereby produce a high potential during the voltage contrast inspection. Both open and short defects causes two adjacent lines to have a same potential during the voltage inspection.

Unfortunately, conventional voltage contrast test structures have associated disadvantages. For example, at least two photolithography masking steps are required to fabricate these test structures. One masking step is required for creating the contacts to the substrate, which is grounded, and another masking step is required for fabricating the metal layer of the test structure which is being tested. The time required to fabricate a conventional voltage contrast test structure could be important in some applications, such as using the voltage contrast based test structures for quickly qualifying and/or monitoring a process tool's status.

Another more significant deficiency of the conventional voltage contrast test structures is that they can only detect hard opens and shorts. This becomes an extremely significant issue, for example, in Cu metallization processing because a significant percentage of the defects are partial opens. These partial opens, in vias or in metal lines, are a reliability concern and also degrade the parametric performance of the semiconductor chip.

Accordingly, there is a need for improved test structures which may be quickly fabricated. Additionally, there is a need for improved test structures in which partial open and short defects may be detected.

SUMMARY

In one embodiment of the present invention, an improved voltage contrast test structure are provided. In general terms, the test structure can be fabricated in a single photolithography step or with a single reticle or mask. The test structure includes substructures which are designed to have a particular voltage potential pattern during a voltage contrast inspection. For example, when an electron beam is scanned across the test structure, an expected pattern of intensities are produced and imaged as a result of the expected voltage potentials of the test structure. However, when there is an unexpected pattern of voltage potentials present during the voltage contrast inspection, this indicates that a defect is present within the test structure. To produce different voltage potentials, a first set of substructures are coupled to a relatively large conductive structure, such as a large conductive pad, so that the first set of substructures charges more slowly than a second set of substructures that are not coupled to the relatively large conductive structure. Mechanisms for fabricating such a test structure are also disclosed. Additionally, searching mechanisms for quickly locating defects within such a test structure, as well as other types of voltage contrast structures, during a voltage contrast inspection are also provided.

In one embodiment, a test structure that is designed for voltage contrast inspection is disclosed. The test structure includes a first substructure having a plurality of floating conductive structures that are designed to charge to a first potential during a voltage contrast inspection and a second substructure that is coupled with a conductive structure having a size selected to cause the second substructure to charge to a second potential that differs from the first potential during the voltage contrast inspection. In one preferred embodiment, the first and second substructure are formed in a single photolithography step.

In one implementation, the first and second substructure are not coupled to the substrate. In another aspect, the first and second substructure are both on a same level. In a specific embodiment, the second substructure includes a plurality of parallel strip segments that are each adjacent to a one of the conductive lines of the first substructure. In a further aspect, the second substructure forms a serpentine shape.

In another implementation, the second substructure is designed to charge more slowly than the first substructure during a voltage contrast inspection. In another aspect, the second substructure is designed to have a different intensity level than the first substructure during a voltage contrast inspection. Preferably, the conductive structure of the second substructure has a size selected so that a partial open may be detected within the second substructure during the voltage contrast inspection. In an alternative embodiment, a method of fabricating one or more of the above described test structure embodiments is also disclosed. The test structure is designed for voltage contrast inspection.

In another embodiment, the invention pertains to a method of inspecting a test structure. Two or more initial portions of the test structure are initially scanned with a charged particle beam to determine whether there is a defect present within the test structure based on whether there is an unexpected pattern of voltage potentials present within the test structure as a result of the initial scanning. When a defect is present, one or more potential defect portions of the test structure are sequentially stepped to, and the one or more potential defect portions of the test structure are scanned with a charged particle beam to thereby locate the defect.

In one implementation, the stepping is in the form of a binary search pattern for locating the defect. In another implementation, the operation of initially scanning two or more initial portions of the test structure with a charged particle beam to determine whether there is a defect present is accomplished by scanning a first end of the test structure to obtain a first potential for the first end, scanning a second end of the test structure to obtain a second potential for the second end, and determining that the test structure has an open defect when the first end potential differs from the second end potential.

In another aspect, the operation of stepping to one or more potential defect portions of the test structure and scanning the one or more potential defect portions of the test structure with a charged particle beam to thereby locate the defect includes a) stepping to a first current portion of the test structure and scanning the first current portion of the test structure for a defect, b) when the defect is not found and a transition in intensity occurs between the previous scan and current scan, stepping to a next portion of the test structure that is between the previous scan and the current scan, and c) when the defect is not found and a transition in intensity does not occur between the previous scan and current scan, stepping to a next portion of the test structure that is not between the previous scan and the current scan. In one aspect, the next portion is halfway between the previous and current scan when the defect is not found and a transition in intensity occurs between the previous scan and current scan, and the next position is halfway between the current scan and an end of the test structure that is not between the previous and current scan when defect is not found and a transition in intensity does not occur between the previous scan and current scan. In a further aspect, it is determined whether the current scan includes a transition in intensity point for the current scan that is not the defect, and the stepping to the next portion operation is performed in a new direction when the current scan includes the transition in intensity point that is not the defect. In one implementation, the new direction of the next scan is perpendicular to a direction of the previous scan. In a specific aspect, operation (b) and (c) are repeated until the defect is found.

In one embodiment, the defect can be an open defect, and the open defect is found when a transition in intensity occurs within the test structure itself. In a further embodiment, the open defect can be a partially open defect. In another implementation, the defect can be a short defect and the defect is found when a physical short is found within the test structure.

In another embodiment, the invention pertains to an inspection system for detecting defects within a test structure. The system includes a beam generator for generating an electron beam, a detector for detecting electrons, and a controller arranged to perform one or more of the above described methods.

These and other features of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general terms, one embodiment of the present invention provides voltage contrast based test structures that can be fabricated in a single photolithography masking step and/or can be used to detect partial opens. In one implementation, the test structure contains at least two substructures. The two substructures are designed to produce different voltage contrast intensities without having to couple one of the substructures to ground (e.g., to the substrate).

Figure 1:
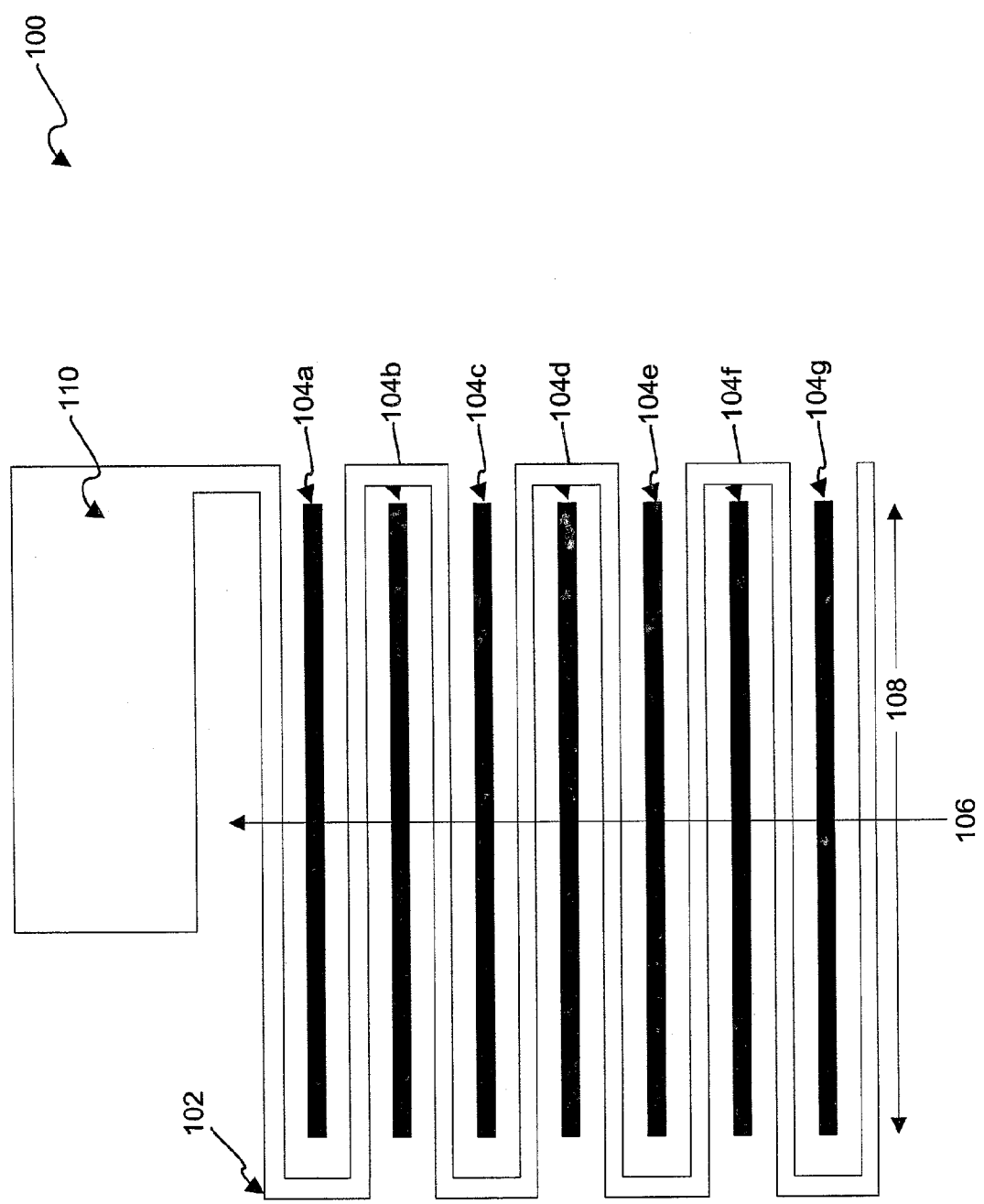
FIG. 1 is a diagrammatic top view representation of a voltage contrast image of a test structure in accordance with one embodiment of the present invention.

FIG. 1 is a diagrammatic top view representation of a voltage contrast image of a test structure 100 in accordance with one embodiment of the present invention. As shown, the test structure includes a first substructure 102 that is coupled with a large conductive pad 110 and a second substructure 104 formed from a plurality of floating conductive lines (e.g., 104a through 104g). Although the first substructure is described as being coupled with a large conductive pad, of course, any suitable conductive structure may be used that results in a different potential being produced in the first substructure during a voltage contrast scan, as compared in the second substructure. Since the first and second substructures are formed within the same conductive layer, the entire test structure may be fabricated with a single photolithography step. Photolithography techniques are well known to those skilled in the art.

The large conductive pad 110 of the first substructure has a size that is selected to result in a different potential and intensity (i.e., in secondary and backscattered electrons) when scanned with an electron beam, as compared with the second substructure. That is, the large conductive pad 110 is sized so that the first substructure to which it is coupled charges differently than the second substructure that is not coupled to the pad 110. Different amounts of secondary or backscattered electrons are emitted from the differently charged portions of the test structure in response to the incident electron beam. In the illustrated embodiment, the conductive lines 104a through 104g of the second substructure charge quickly and produce a dark image during the voltage contrast scan. In this case, the pad 110 is sized so that the first substructure 102 charges more slowly than the conductive lines of the second substructure 104. Thus, the conductive pad 110 and the first substructure 102 together have an area that is significantly larger than the area of a single one of the conductive lines (e.g., 104a) of the second test structure. The size of the conductive pad 110 may be determined experimentally or by simulation. For example, increasing sizes may be used for various conductive pads of test structures to determine whether the test structure's two substructures produce different potentials during voltage contrast inspection. Thus, the size of the conductive pad 110 may be selected to be equal to or greater than the smallest sized conductive pad 110 that experimentally produced differing potentials.

As an electron beam is passed over these substructures 102 and 104 (e.g., in direction 106), the substructure 102 that is connected to the large metal pad 110 has a potential that charges slowly compared to a structure that is not connected to a large metal pad. Thus, the large metal pad acts as a virtual ground and appears bright, while the floating conductive lines of the second substructure 104 appear dark. After the beam scans the substructure 102 for a period of time, the substructure 102 will approach the same potential as the second substructure 104 that is not connected to the large metal pad. Hence, the voltage contrast difference is transient in nature. However, as an electron beam is scanned initially, for example, in direction 206 along width 208, the test structure appears as alternating dark and light substructures when there is no defect present.

Figure 2A:
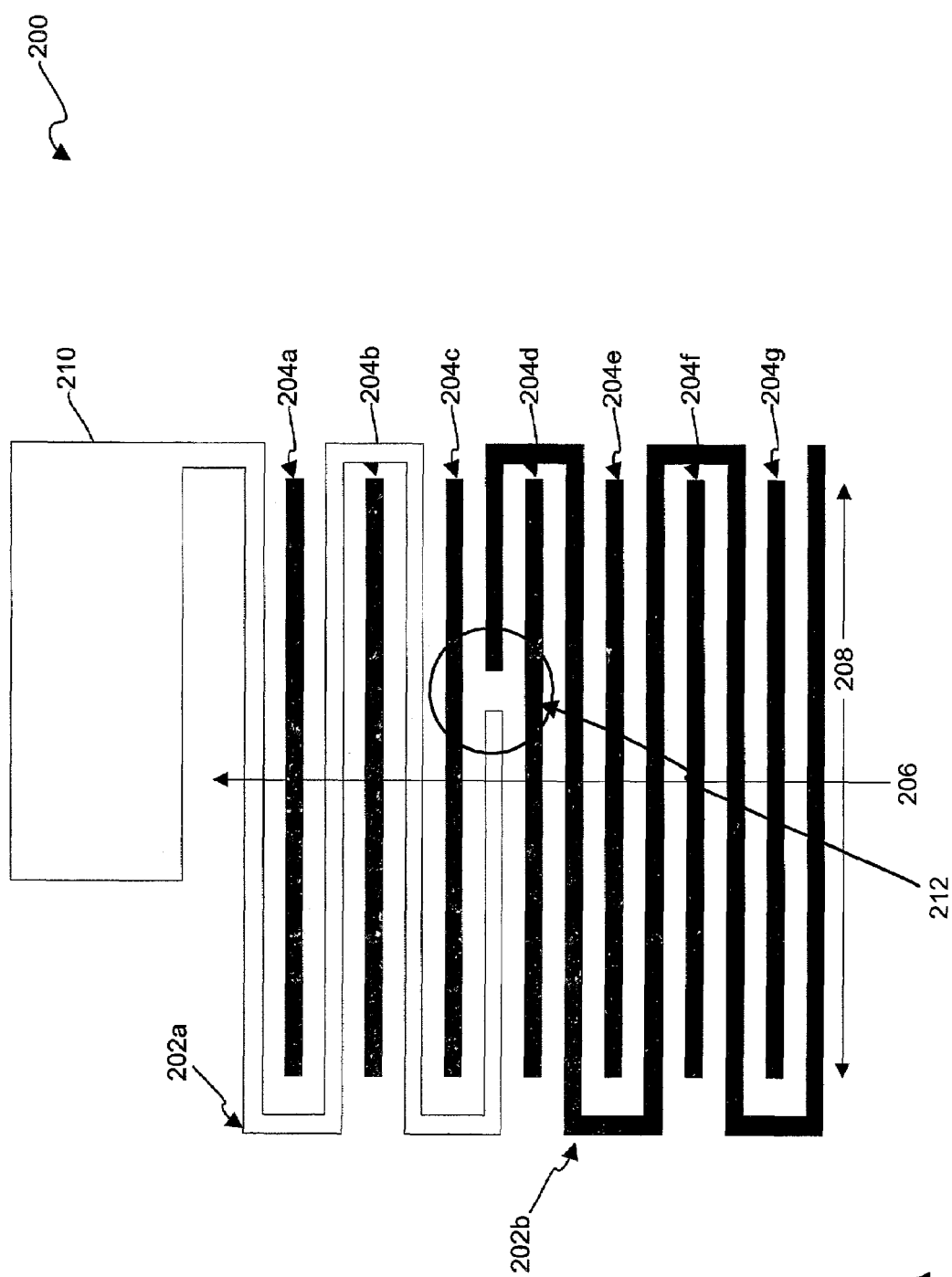
FIG. 2A is a diagrammatic top view representation of a voltage contrast image of a test structure having an open defect in accordance with one embodiment of the present invention.

FIG. 2A is a diagrammatic top view representation of a voltage contrast image of a test structure 200 having an open defect 204 in accordance with one embodiment of the present invention. The test structure 200 of FIG. 2 is similar to the test structure 100 of FIG. 1, except that the test structure 200 of FIG. 2 has an open defect 212. More specifically, the test structure 200 of FIG. 2 includes a first substructure 202 that has the open defect 212 and a second substructure 204 that does not include a defect. The first substructure includes a first portion 202a that remains coupled to a conductive pad 210 and a second portion 202b that is not coupled to the conductive pad 210.

Although transient in nature, one can detect an open defect within the first substructure 202. During a scan the portion 202a of the first substructure connected to the conductive pad 210 has a different potential then the portion 202b of the substructure 202 that is not connected to the large conductive pad 110. Hence, the structure displays voltage contrast at the point of the physical break 212. In other words, when an electron beam is scanned, for example, in direction 206 along width 208, the test structure 200 does not have alternating dark and light substructures as expected. The transient potential difference between the two different portions 202a and 202b of the first substructure may be characterized as an open defect.

The same principle can be employed for detecting partial opens with the first substructure 202. Partial opens increase the resistance of the metal path. Consequently, under electron beam scanning, the paths to the pad 210 that contain a partial open will develop transient potential differences compared to the paths to the pad 210 which do not have a partial open defect. This transient potential difference can be detected as a transient voltage contrast signal. This transient potential difference may be determined to be a partial open defect.

If the initial scan width 208 includes the defect, the specific location of such defect may then be determined by determining where the first substructure transitions between different potentials. Alternatively, if the initial scan width did not contain the defect, a second scan may be required, for example, along a direction perpendicular to the first scan to determine the defect's specific location. Any suitable techniques for determining a defect's presence and such defect's specific position may be utilized. Several defect presence detection and defect location techniques are described in co-pending (1) U.S. patent application Ser. No. 09/648,380, entitled TEST STRUCTURES AND METHODS FOR INSPECTION OF SEMICONDUCTOR INTEGRATED CIRCUITS, filed Aug. 25, 2000, by Akella V. S. Satya et al., (2) U.S. patent application Ser. No. 09/999,843, entitled APPARATUS AND METHODS FOR MONITORING SELF-ALIGNED CONTACT ARRAYS, filed Oct. 24, 2001, by Kurt H. Weiner et al., (3) U.S. patent application Ser. No. 10/000,114, entitled APPARATUS AND METHODS FOR RELIABLE AND EFFICIENT DETECTION OF VOLTAGE CONTRAST DEFECTS, filed Jun. 29, 2001, by Kurt H. Weiner et al., (4) U.S. patent application No. 09/991,188, entitled APPARATUS AND METHODS FOR PREDICTING MULTIPLE PRODUCT CHIP YIELDS THROUGH CRITICAL AREA MATCHING, filed Nov. 14, 2001, by Kurt H. Weiner et al., and (5) U.S. Provisional Application, having an application No. 60/329,804, entitled APPARATUS AND METHODS FOR SEMICONDUCTOR IC FAILURE DETECTION, filed Oct. 17, 2001, by Kurt H. Weiner et al. These applications are incorporated herein by reference in their entirety. Additionally, other types of test structures may be easily modified to implement the present invention. That is, any suitable voltage contrast type test structure may be modified so that a first substructure is coupled with a relatively large conductive structure, instead of being coupled to the substrate. Several suitable test structures are also described in detail in the above referenced patent applications (1) through (5).

Figure 2B:
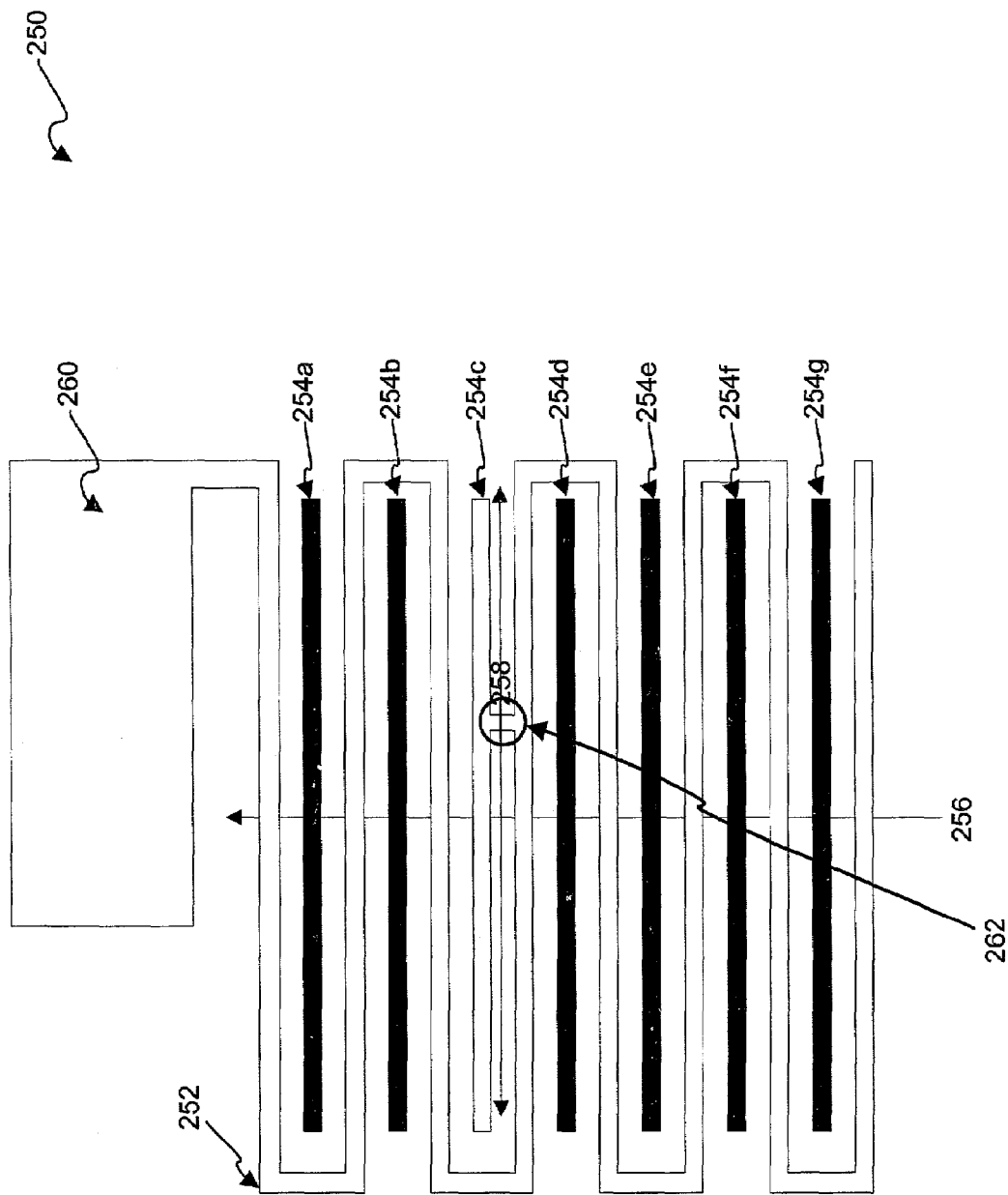
FIG. 2B is a diagrammatic top view representation of a voltage contrast image of a test structure having a short defect in accordance with one embodiment of the present invention.

FIG. 2B is a diagrammatic top view representation of a voltage contrast image of a test structure 250 having a short defect 262 in accordance with one embodiment of the present invention. As shown, the test structure includes a serpentine substructure 252 coupled with a large conductive pad 260. The test structure also includes a plurality of conductive line substructures 254, which are designed to remain floating or not coupled to the large conductive pad 560. However, a short defect 262 has occurred between the serpentine substructures 252 and the conductive line 254c. During a voltage contrast scan in direction 256, the substructures are expected to have alternating potentials which result in alternating bright and dark lines. However, when two adjacent lines have a same potential, it is determined that there is a defect in one of the substructures. As shown, the conductive line 254c has the same potential and brightness level as adjacent strips of the serpentine substructure 252. The short 262 may be found by scanning along direction 258.

In particular types of voltage contrast test structures, a defect's position may be determined by performing a search that minimizes search time. In one embodiment of the present invention, a defect may be located by stepping to various locations on the test structure, rather than continuously scanning along, for example, the entire length of the test structure. At each step location, the test structure is scanned by the electron beam (e.g., rastered). This "accelerated search" technique may be implemented on any suitable test structure, in addition to the above described test structures with large conductive structures. One example of such an accelerated search is a binary search. Of course, any suitable search step may be utilized to quickly "step" to the defect's location in one or more steps. For example, the electron beam may be moved relative to the test structure in predefined incremental distances.

Figure 3A:
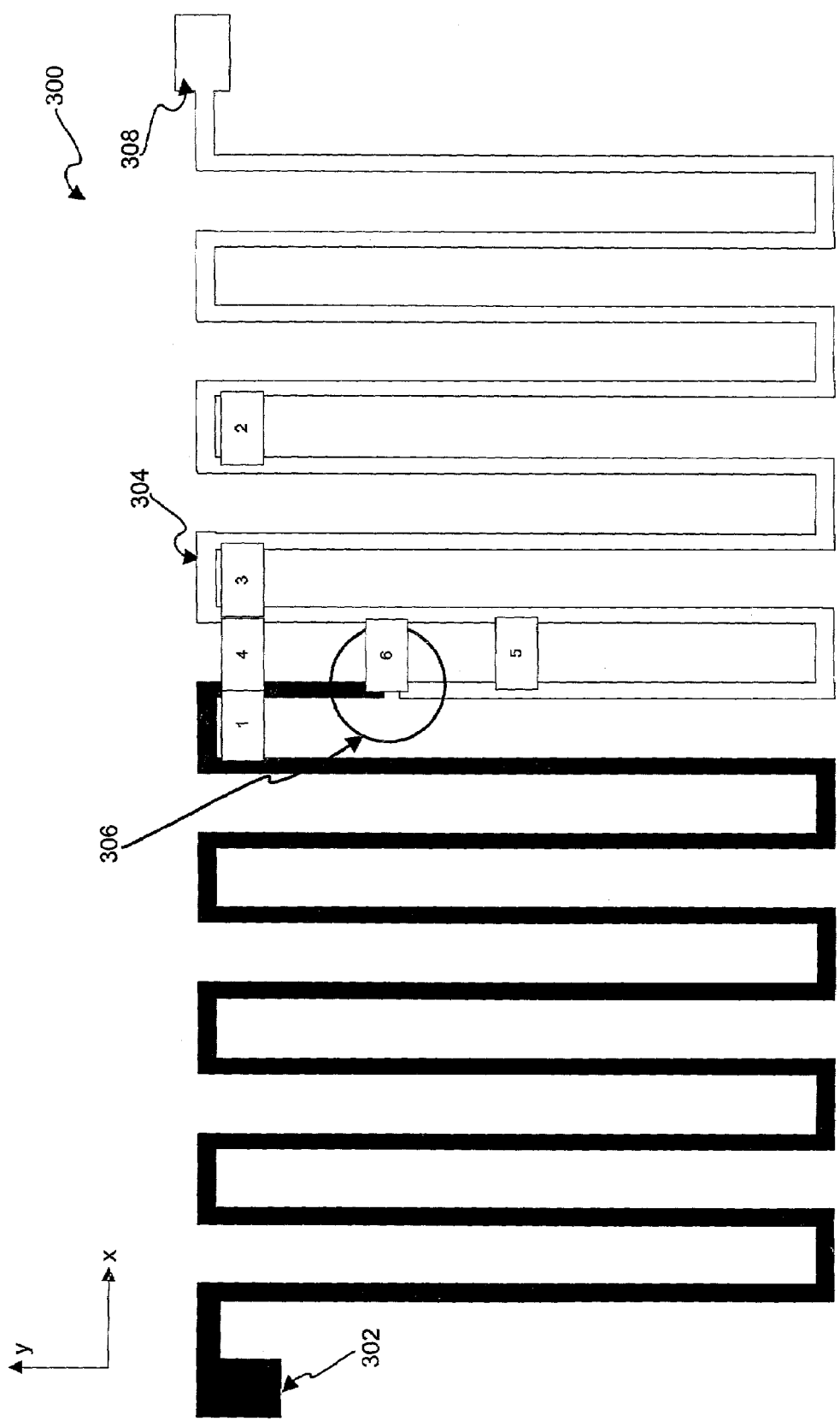
FIG. 3A illustrates a binary search mechanism for locating an open type defect in a test structure in accordance with one embodiment of the present invention
Figure 3B:
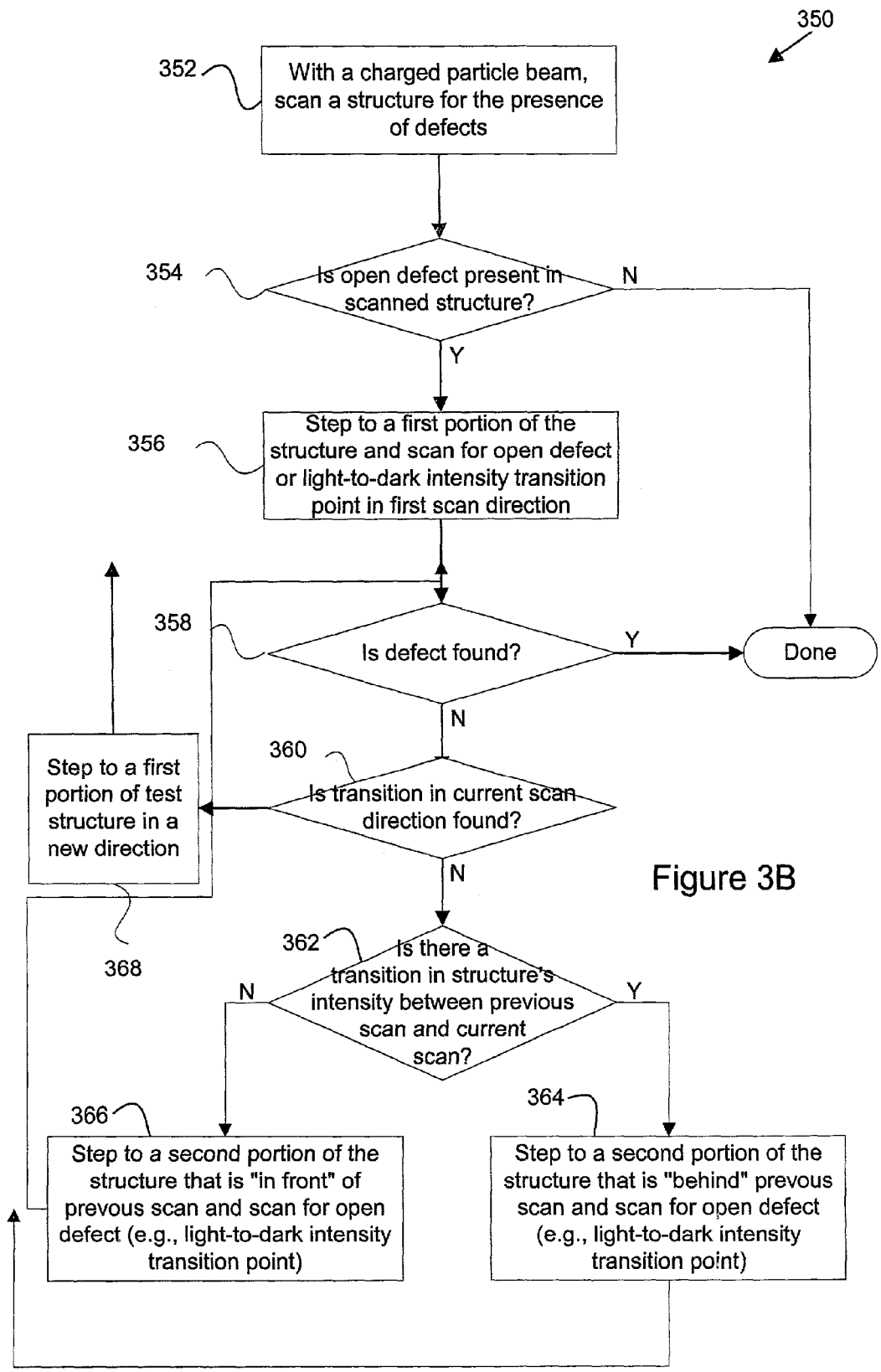
FIG. 3B is a flowchart illustrating a procedure for locating a defect in accordance with one embodiment of the present invention.

FIG. 3A illustrates a binary search mechanism for locating an open type defect in a test structure 300 in accordance with one embodiment of the present invention. FIG. 3B is a flowchart illustrating a procedure for locating a defect in accordance with one embodiment of the present invention. FIGS. 3A and 3B will be described in conjunction. The test structure is grounded, for example, at target pad 302. Initially, it is determined whether an open defect is present with the test structure 300 by scanning the structure with a charged particle beam in operations 352 and 354. For example, the potential of target pad 302 is compared with the potential of reference pad 308 during a voltage contrast inspection. When the pads differ in potential, it is determined that an open defect is present within the test structure 300. When the pads have the same potential, it is determined that there is no defect present.

When it is determined that the test structure has no defects present, the procedure 350 ends. When a defect's presence is found, the charged particle beam is stepped relative to the structure to a first portion of the structure to scan for an open defect in operation 356. For example, it is determined whether there is a light-to-dark intensity transition point in the test structure itself, which indicates an open defect's location. In the illustrated embodiment of FIG. 3A, a binary search for the defect is first performed along the x direction. Although the test structure is scanned along the top portion, any portion of the test structure may be scanned during the search. The electron beam is moved relative to the sample to location "1", which is in the middle of the test structure 300 along the x direction. It is then determined whether an open defect has been found in operation 358. In the illustrated embodiment, it is determined whether the defect has been found by determining whether the transition point in the test structure itself has been found. If the defect has been found, the procedure ends.

If the defect has not been found, it is then determined whether an intensity transition between dark and bright has occurred in the scan direction between the previous and current scan in operation 360. This determination is based on whether a transition point within the "scan direction" has been found, not whether the transition point has been found in the test structure itself. For example, the test structure may include a dark portion immediately followed by a light portion along the x direction, but the transition point within the test structure itself has not been found yet.

If the transition point in the scan direction has not been found yet, it is then determined whether there is a transition in the test structure between the previous and current scan in operation 362. For instance, it is determined whether there is a transition between target pad 302 and current scan location 1. If it is determined that there is a transition between the target pad 302 and location 1, then it is determined that the defect is to the left of or "behind" the search location 1. In other words, it is determined that the defect is between the previous (e.g., pad 302) and current scan (e.g., location 1). The charged particle beam is then stepped to "behind" the current scan to a second portion of the test structure and this second portion is then scanned for an open defect in operation 364. Otherwise, the charged particle beam is then stepped in "front of" the current scan to a second portion of the test structure and this second portion is then scanned for an open defect in operation 366.

The terms "behind" and "in front of" are used herein as a position relative to the current stepping direction. For example, if the beam has stepped from the test pad 302 to location 1 in a +x direction, the beam moves to a position "behind" location 1 when it is moved in the −x direction. In contrast, the beam moves to a position "in front of" location 1 when it is moved in the +x direction, which is in the same direction as the current stepping direction defined by moving the beam from the pad 302 to location 1.

Since the transition does not occur between locations 1 and the target pad, the electron beam then moves relative to the test structure to a location 2 that is halfway between location 1 and the rightmost end of test structure (operation 364). The procedure then repeats operation 358 to determine whether the defect has been found. In this example, it is determined that the defect has not been found. It is then determined that the transition point in the scan direction has not been found in operation 360. It is then determined that the transition is between the current scan and the previous scan in operation 362. As shown, a transition in brightness level has occurred between locations 1 and 2. The electron beam then moves relative to the sample to a location 3 which is to the left of location 2 and halfway between locations 1 and 2 to scan for an open defect (operation 364) at location 3. Since no defect is found at location 3 and it is determined that the transition is between location 3 and 1 (i.e., not between the previous and current scan), the electron beam then moves to location 4 which is to the left or "in front" of position 3 and halfway between locations 3 and 1 (operation 362). The transition in the x direction is also found at location 4.

After the brightness transition is found in a first direction, the electron beam is then moved relative to the test structure in a binary search along the y direction to find the location of the defect in operation 368. As shown, the electron beam is first moved relative to the test structure halfway down the length of the test structure to location 5. Since the brightness has transitioned between bright and dark from location 4 to 5, the next location 6 is halfway between locations 5 and 4. The actual transition point in the test structure itself is found at location 6. It may then be determined that the transition point is the location of the open defect.

In an alternative embodiment, a test structure may be scanned continuously in a first direction to detect the presence of a defect. In the test structure of FIG. 1, a charged particle beam is scanned continuously in direction 108. It is then determined whether there are alternating dark and bright of intensity levels for the conductive strips of the test structure. An alternating pattern of intensity pattern indicates that there is no defect present. However, when two adjacent strips have a same brightness level, it is determined that there is a defect present within on the adjacent strips having the same brightness level. The defect's location may then be determined using a stepping search algorithm, such as a binary search, along direction 106 as described above with relation to FIGS. 3A and 3B. An open defect's position is found when there is a transition in a strip from dark to light intensity value, or visa versa. A short defect is found when the physical short is found between the two strips.

Figure 4:
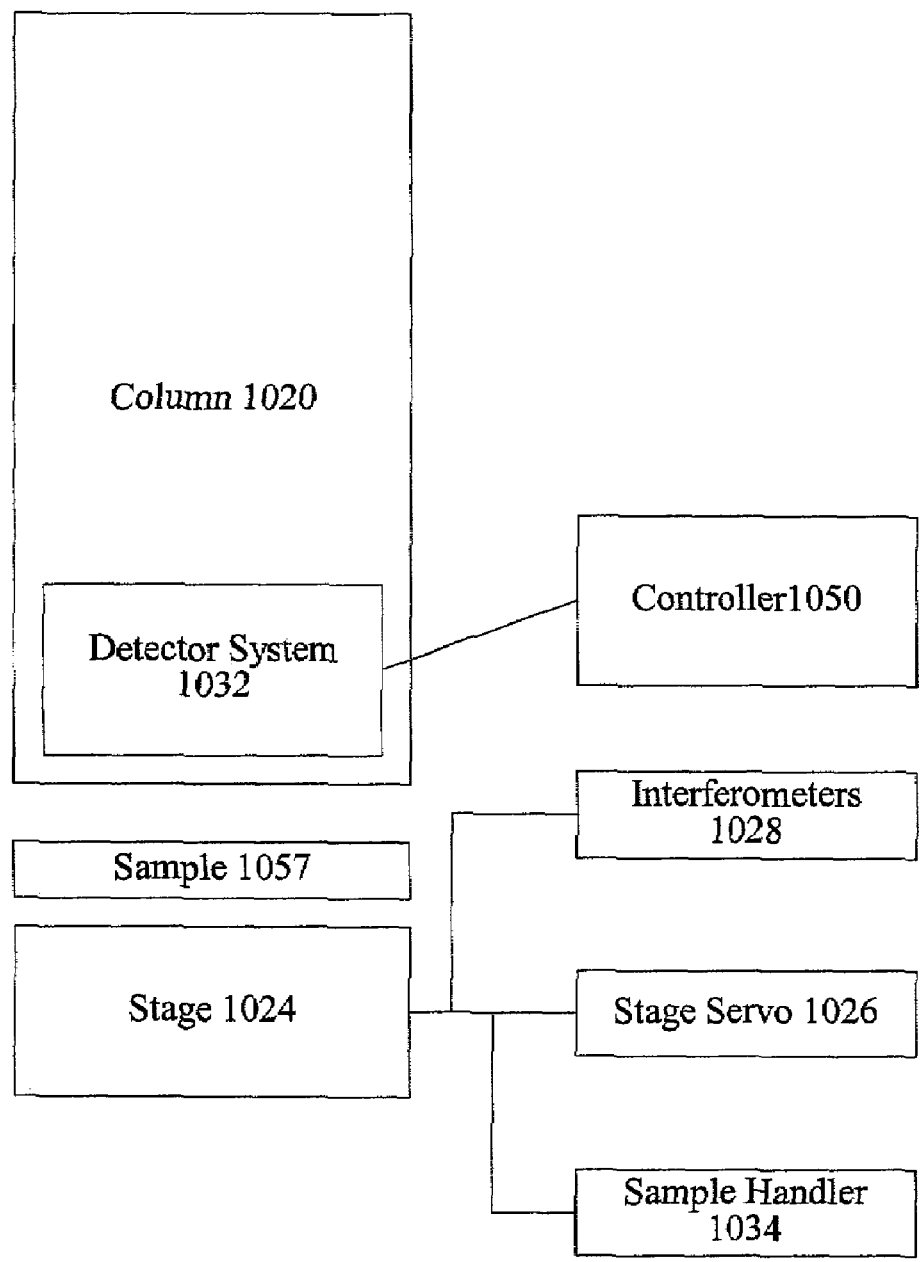
FIG. 4 is a diagrammatic representation of a system in which the techniques of the present invention may be implemented.

FIG. 4 is a diagrammatic representation of a scanning electron microscope (SEM) system in which the techniques of the present invention may be implemented. The detail in FIG. 4 is provided for illustrative purposes. One skilled in the art would understand that variations to the system shown in FIG. 4 fall within the scope of the present invention. For example, FIG. 4 shows the operation of a particle beam with a continuously moving stage. However, the test structures and product structures and many of the inspection techniques described herein are also useful in the context of other testing devices, including particle beams operated in step and repeat mode. As an alternative to moving the stage with respect to the beam, the beam may be moved by deflecting the field of view with an electromagnetic lens. Alternatively, the beam column to be moved with respect to the stage.

Sample 1057 can be secured automatically beneath a particle beam 1020. The particle beam 1020 can be a particle beam such as an electron beam. The sample handler 1034 can be configured to automatically orient the sample on stage 1024. The stage 1024 can be configured to have six degrees of freedom including movement and rotation along the x-axis, y-axis, and z-axis. In a preferred embodiment, the stage 1024 is aligned relative to the particle beam 1020 so that the x-directional motion of the stage is corresponds to an axis that is perpendicular to a longitudinal axis of inspected conductive lines. Fine alignment of the sample can be achieved automatically or with the assistance of a system operator. The position and movement of stage 1024 during the analysis of sample 1057 can be controlled by stage servo 1026 and interferometers 1028. While the stage 1024 is moving in the x-direction, the inducer 1020 can be repeatedly deflected back and forth in the y direction. According to various embodiments, the inducer 1020 is moving back and forth at approximately 100 kHz. Alternatively, a relatively wide beam may be used to scan across a particular swath or area of the test structure without rastering of the beam.

A detector 1032 can also be aligned alongside the particle beam 1020 to allow further defect detection capabilities. The detector 1032 as well as other elements can be controlled using a controller 1050. Controller 1050 may include a variety of processors, storage elements, and input and output devices. The controller may be configured to implement the defect detection and location techniques of the present invention. The controller may also be configured to correlate the coordinates of the electron beam with respect to the sample with coordinates on the sample to thereby determine, for example, a location of a determined defect. In one embodiment, the controller is a computer system having a processor and one or more memory devices.

Regardless of the controller's configuration, it may employ one or more memories or memory modules configured to store data, program instructions for the general-purpose inspection operations and/or the inventive techniques described herein. The program instructions may control the operation of an operating system and/or one or more applications, for example. The memory or memories may also be configured to store images of scanned samples, reference images, defect classification and position data, as well as values for particular operating parameters of the inspection system.

Because such information and program instructions may be employed to implement the systems/methods described herein, the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave travelling over an appropriate medium such as airwaves, optical lines, electric lines, etc. Examples of program instructions include both machine code, such as produced by a compiler, and files containing higher level code that may be executed by the computer using an interpreter.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A method of inspecting a test structure, comprising:
   initially scanning two or more initial portions of the test structure with a charged particle beam to image the initial portions and determine whether there is a defect present within a plurality of potential defect portions that have different locations than the initial portions based on whether there is an unexpected pattern of one or more intensity levels within the imaged initial portions, wherein the potential defect portions are not scanned by the particle beam during the initial scanning; and
   when the initial scanning results in a determination that a defect is present in one or more of the potential defect portions, sequentially stepping to one or more of the potential defect portions of the test structure and scanning the one or more potential defect portions of the test structure with a charged particle beam to thereby image the one or more potential defect portions and locate the defect, wherein the defect is located when an unexpected pattern of one or more intensity levels are present within a one of the imaged potential defect portions.

2. A method as recited in claim 1, wherein the stepping is in the form of a binary search pattern for locating the defect.

3. A method as recited in claim 1, wherein initially scanning two or more initial portions of the test structure with a charged particle beam to determine whether there is a defect present is accomplished by:
   scanning a first end of the test structure to obtain a first intensity level for the first end;
   scanning a second end of the test structure to obtain a second intensity level for the second end; and
   when the first end intensity level differs from the second end intensity level, determining that the test structure has an open defect.

4. A method as recited in claim 1, wherein the stepping to one or more potential defect portions of the test structure and scanning the one or more potential defect portions of the test structure with a charged particle beam to thereby locate the defect comprises:
   a) stepping to a first current portion of the test structure and scanning the first current portion of the test structure for a defect;
   b) when the defect is not found and a transition in intensity occurs between the previous scan and current scan, stepping to a next portion of the test structure that is between the previous scan and the current scan; and
   c) when the defect is not found and a transition in intensity does not occur between the previous scan and current scan, stepping to a next portion of the test structure that is not between the previous scan and the current scan.

5. A method as recited in claim 4, wherein the next portion is halfway between the previous and current scan when the defect is not found and a transition in intensity occurs between the previous scan and current scan, and the next position is halfway between the current scan and an end of the test structure that is not between the previous and current scan when defect is not found and a transition in intensity does not occur between the previous scan and current scan.

6. A method as recited in claim 5, the method further comprising determining whether the current scan includes a transition in intensity point for the current scan that is not the defect, wherein the stepping to the next portion operation is performed in a new direction when the current scan includes the transition in intensity point that is not the defect.

7. A method as recited in claim 6, wherein the new direction of the next scan is perpendicular to a direction of the previous scan.

8. A method as recited in claim 4, repeating operation (b) and (c) until the defect is found.

9. A method as recited in claim 4, wherein the defect can be an open defect and the defect is found when a transition in intensity occurs within the test structure itself.

10. A method as recited in claim 9, wherein the open defect can be a partially open defect.

11. A method as recited in claim 4, wherein the defect can be a short defect and the defect is found when a physical short is found within the test structure.

* * * * *